US 6,555,134 B1

United States Patent
Aviram et al.

(10) Patent No.: US 6,555,134 B1
(45) Date of Patent: Apr. 29, 2003

(54) SYNERGISTIC MIXTURES OF GARLIC AND LYCOPENE FOR PREVENTING LDL OXIDATION

(75) Inventors: Michael Aviram, Haifa (IL); Bianca Fuhrman, Haifa (IL); Zohar Nir, Beer Sheva (IL); Jeorg Gruenwald, Berlin (DE)

(73) Assignee: Lycored Natural Products Industries Ltd., Beer Sheva (IL)

( * ) Notice: Subject to any disclaimer, the term of this patent is extended or adjusted under 35 U.S.C. 154(b) by 0 days.

(21) Appl. No.: 09/601,403

(22) PCT Filed: Jan. 31, 1999

(86) PCT No.: PCT/IL99/00062

§ 371 (c)(1),
(2), (4) Date: Oct. 11, 2000

(87) PCT Pub. No.: WO99/38518

PCT Pub. Date: Aug. 5, 1999

(30) Foreign Application Priority Data

Feb. 1, 1998 (IL) .................................................. 123132

(51) Int. Cl.[7] .............................. A61K 9/20; A61K 9/48; A61K 35/78
(52) U.S. Cl. ....................... 424/456; 424/439; 424/464; 424/484; 424/725; 424/754
(58) Field of Search ................................ 424/464, 451, 424/456, 484, 439, 725, 754

(56) References Cited

U.S. PATENT DOCUMENTS 5,883,086 A 3/1999 Craft 5,904,924 A 5/1999 Gaynor et al.

FOREIGN PATENT DOCUMENTS

WO WO 98 33494 8/1998

OTHER PUBLICATIONS

Warshafsky et al., "Effect of Garlic on Total Serum Cholesterol", *Ann. Intern. Med.*, vol. 119, pp. 599–605, (1993).
Kenzelmann et al., "Limitation of the Deterioration of Lipid Parameters by a Standardized Garlic–Ginkgo Combination Product", *Arzneimettelforschung*, vol. 43, pp. 978–981, (1993).
Auer et al., "Hypertension and hyperlipidaemia: garlic helps in mild cases", *the British Journal of Clinical Practice—Supplement*, vol. 69, pp. 3–6, (1990).
Mader et al., "Treatment of Hyperlipidaemia with Garlic–powder Tablets", *Arzneimittelforschung*, vol. 40, pp. 1111–1116, (1990).
Vorberg e al., "Therapy with garlic: result of a placebo–controlled, double–blind study", *The British Journal of Clinical Practice–Supplement*, vol. 69, pp. 7–11, (1990).
Gebhardt, "Multiple Inhibitory Effects of Garlic Extracts on Cholesterol Biosynthesis in Hepatocytes", *Lipids*, vol. 28, No. 7, (1993).

(List continued on next page.)

*Primary Examiner*—James M. Spear
(74) *Attorney, Agent, or Firm*—Browdy and Neimark, P.L.L.C.

(57) ABSTRACT

The present invention provides a synergistic pharmaceutical or dietary composition containing lycopene and garlic. The present invention also provides an improved method to block the oxidation of LDL in order to arrest the process of therapeutic agent and a method for the prevention or treatment of atheroscelerosis using and/or applying said compositions.

40 Claims, 6 Drawing Sheets

OTHER PUBLICATIONS

Warshafaky et al., "Effect of Garlic on Total Serum Cholesterol", *Ann Intern Med.*, vol. 119, pp. 599–605, (1993).

Jain et al., "Can Garlic Reduce Levels of Serum Lipids? A Controlled Clinical Study", *The American Journal of Medicine*, vol. 94, pp. 632–635, (1993).

Kleijnen et al., "Garlic, Onions and Cardiovascular risk factors. A review of the evidence from human experiments with emphasis on commercially available preparations", *Br. J. Clin. Pharmac*, vol. 28, pp. 535–544, (1989).

Silagy et al., "Garlic as a lipid lowering agent a meta analysis", *Journal of the Royal College of Physicians of London*, vol. 28, No. 1, pp. 39–45, (1994).

Neil et al., "Garlic powder on the treatment of moderate hyperlipidaemia: a controlled trial and meta–analysis", *Journal of the Royal College Physicians of London*, vol. 30, No. 4, pp. 329–334, (1996).

Sendl et al., "Inhibitions of cholesterol synthesis in vitro by extracts and isolated compounds prepared from garlic and wild garlic", *Atherosclerosis*, vol. 94, pp. 79–95, (1992).

Barton Duell, "Prevention of Atherosclerosis with Dietary Antioxidants: Fact or Fiction?", The Journal of Nutrition, vol. 126, No. 4, pp. 1067–1071, Apr. 1996.

S. Lata Et Al., "Beneficial Effects of *Allium sativum, Allium cepa* and *Commiphora mukul* on Experimental Hyperlipidemia and Atherosclerosis– A comparative Evaluation", Journal of Postgraduate Medicinevol. 37, No. 3, pp. 132–135, 1991.

H. Heinle and E. Berz, "Effect of Dietary Garlic Supplementation in a Rat Model of Atherosclerosis", Arrneimettelforschung, vol. 44, No. 5, pp. 614–617, 1994.

T. Brosche, Et Al., "The Effect Of A Garlic Preparation On The Composition Of Plasma Lipoproteins And Erythrocyte Membranes in Geriatric Subjects", The British Journal of Clinical Practice–Supplement, vol. 69, pp. 12–19, 1990.

Jayashree Gadkari and Vijaya Joshi, "Effect of Ingestion of Raw Garlic on Serum Cholesterol Level, Clotting Time and Fibrinolytic Activity in Normal Subjects", Journal of Postgraduate Medicine, vol. 37, No. 3, pp. 128–131, 1991.

M. Ali and M. Thomson, "Consumption of a Garlic Clove A Day Could Be Beneficial In Preventing Thrombosis", Prostaglandins Leutkotrienes and Essential Fatty Acids, vol. 53, pp. .221–212, 1995.

Manfred Steiner, Et Al., "A Double–Blind Crossover Study In Moderately Hypercholesterolemic Men That Compared The Effect Of Aged Garlic Extract And Placebo Administration On Blood Lipids", The American Journal of Clinical Nutrition, vol. 64, No. 6, pp. 866–870, 1996.

Rolf Gebhardt and Halgund Beck, "Differential Inhibitory Effects Of Garlic–Derived Organosulfur Compounds On Cholesterol Biosynthesis In Primary Rat Heptocyte Cultures", LIPIDS, vol. 31, No. 12, pp. 1269–1276, 1996.

Agarwal, "Therapeutic Actions of Garlic Constitutes", *Medicinal Research Reviews*, (1998), vol. 16, No. 1, pp. 111–124.

Lawson, "Bioactive Organosulfur Compounds of Garlic and Garlic Products", *Human Medicinal Agents form Plants, American Chemical Society Books*, (1983), pp. 308–330, Washington.

Anonymous, "Deodorized (aged) Garlic Products Versus Conventional Allicin Containing Garlic Products" *Summary of Current Knowledge, Commercial White Paper issued by Wakunanaga of America.*

Eilat et al., "Alteration of lipid profile in hyperlipidemic rabbits by allicin, an active constituent of garlic", *Coronary Artery Disease*, (1995), vol. 6, pp. 985–990.

Gebhardt, "Inhibitions of Cholesterol Biosynthesis by a Water–soluble Garlic Extract in Primary Cultures of Rat Hepatocytes", *Arzneimittelforschung*, (1991), vol. 41, pp. 800–804.

Phelps et al., "Garlic Supplementation and Lipoprotein Oxidation Susceptibility", *Lipids*, (1993) vol. 28, pp. 475–477.

Aviram, "Interaction of Oxidized Low Density Lipoprotein with Macrophages in Atherosclerosis, and the Antiatherogenicity of Antioxidants", *Eur. J. Clin. Chem. Clin. Biochem.*, (1996), vol. 34, pp. 599–608, New York.

Simons et al., "On the effect of garlic on plasma lipids and lipoproteins in mild hypercholesterolaemia", *Atherosclerosis*, (1995), vol. 113, pp. 219–225.

Nir et al., "Lypocene: A New Carotenoid Extracted from Tomatoes", *Food Factors Cancer Prev., Int.*, (1997), pp. 562–564.

Ramon et al., "Antioxidants de la dieta y enfermedad coronaria", *Clinica Cardiovascular*, (1996), vol. 14, No. 2, pp. 29–38.

Stajner et al., "Antioxidant Abilities of Cultivated and Wild Species of Garlic", *Phyotherapy Research*, (1998), vol. 12, pp. S13, John Wiley & Sons, Ltd.

Davies et al., "Atherosclerosis: what is it and why does it occur", *Heart J.*, (1993), vol. 63, pp. S3–S11.

Castelli et al., "Lipids and Risk of Coronary Heart Disease The Framington Study", *Ann. Epidermol.* (1992),ol. 2, No. 1/2, pp. 23–28, Elsevier Science Publishing Co., Inc.

Steinberg et al. "Beyond Cholesterol: Modifications of Low–Density Lipoprotein That Increase Its Atherogenicity", *The New England Journal of Medicine*, (1989), vol. 320, pp. 915–924.

Haberland et al., "The role of altered lipoproteins in the pathogenesis of atherosclerosis", *Am. Heart J.*, (1987), vol. 113, No. 2, pp. 573–577.

Witztum, "The oxidation hypothesis of atherosclerosis", *Lancet*, (1994), vol. 344, pp. 793–795, Department of Medicine, University of California San Diego.

Aviram, "Beyond Cholesterol: Modifications of Lipoproteins and Increased Atherogenicity", *Scientific Press–Florence*, (1993), pp. 15–36, Italy.

Burton, "Antioxidant Action of Carotenoids", *J. Nutr.*, (1989), vol. 119, pp. 109–111, American Institute of Nutrition.

Krinsky, "Antioxidant Functions of Carotenoids", *Free Rad. Biol. Med.*, (1989), vol. 7, pp. 617–635, Pergannon Press, USA.

Kohlmeier et al., "Epidemiologic evidence of a rile of carotenoids in cardiovascular disease prevention", *Am. J. Clin. Nutr.*, (1995), vol. 62, pp. 137S–146S, USA.

Hennekens et al., "Lack of Effect of Long–Term Supplementation with Beta Carotene on the Incidence of Malignant Neoplasms and Cardiovascular Disease", *The New England Journal of Medicine*, (1996) vol. 334, No. 18, pp. 1145–1149, Massachusetts Medical Society.

Fuhrman et al., "Tomato lycopene and β-carotene inhibit low density lipoprotein and its effect depends on the lipoprotein vitamin E content", *Nutr. Metab. Cardiovasc. Dis.*, (1997) vol. 7, pp. 433–443, Medikal Press.

Fuhrman et al., "Hypocholesterolemic Effect of Lycopene and β-Carotene is Related to Suppression of Cholesterol Synthesis and Augmentation of LDL Receptor Activity in Macrophages", *Biochemical and Biophysical Research Communications*, (1997), vol. 233, pp. 658–662, Academic Press.

Derwent Publications Ltd. Database WPI Section Ch, Week 9736; CN1110918.

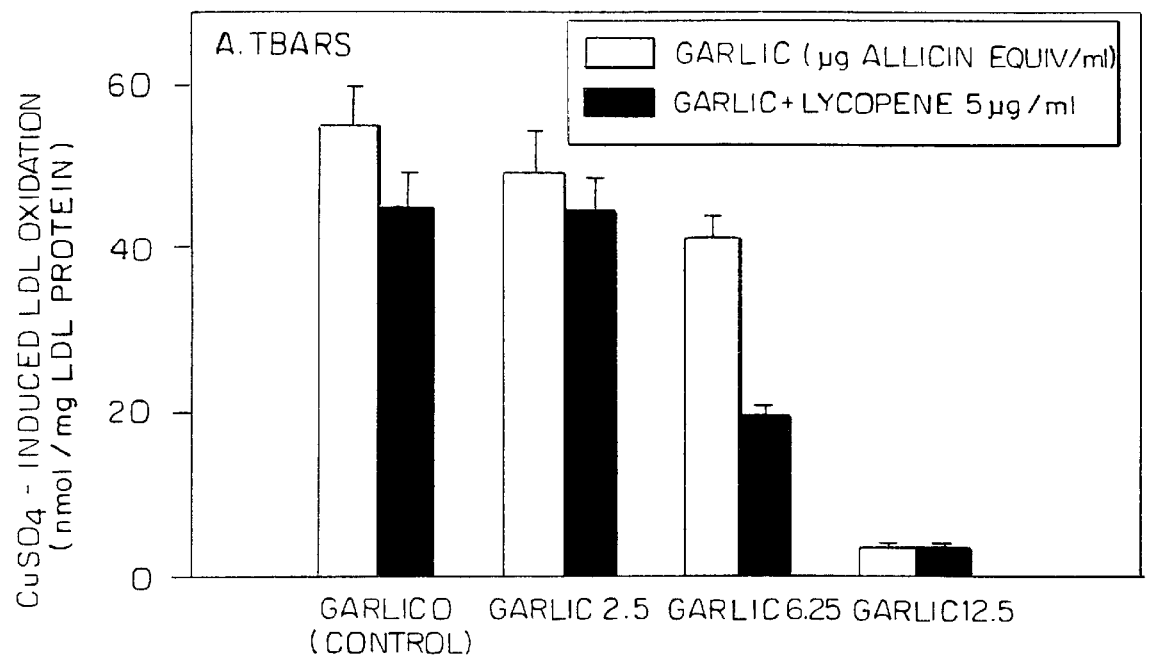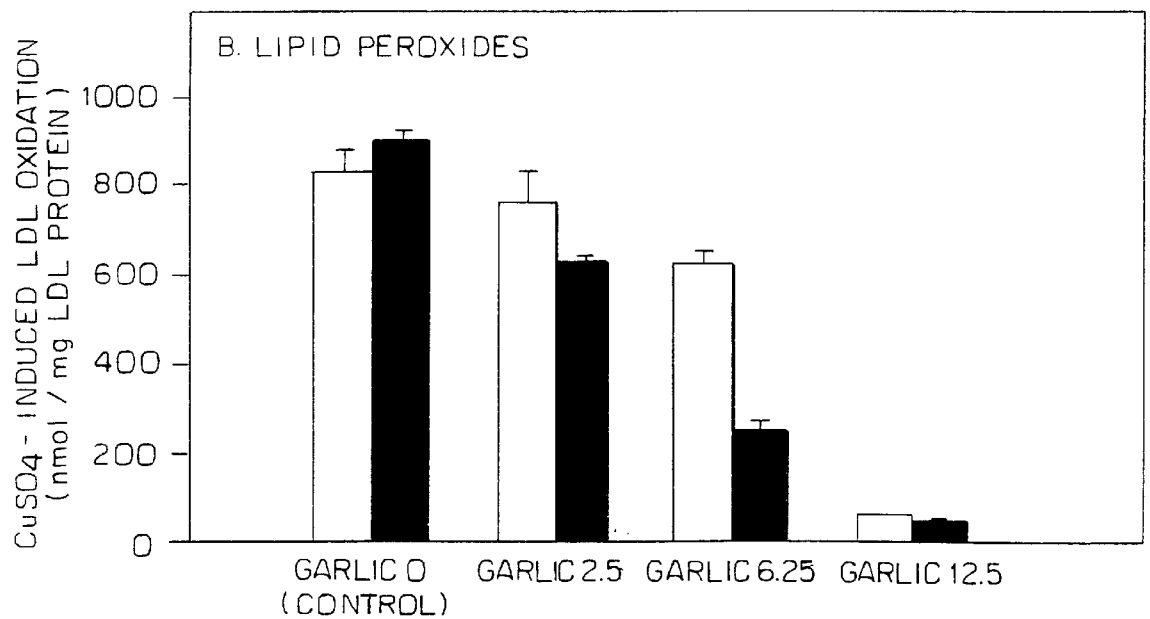

EFFECT OF A COMBINATION OF GARLIC AND TOMATO OLEORESIN ON COPPER IONS-INDUCED LDL OXIDATION

EFFECT OF A COMBINATION OF GARLIC AND TOMATO OLEORESIN ON COPPER IONS-INDUCED LDL OXIDATION

EFFECT OF A COMBINATION OF GARLIC AND LYCOPENE ON COPPER IONS-INDUCED LDL OXIDATION

EFFECT OF A COMBINATION OF GARLIC AND TOMATO OLEORESIN ON COPPER IONS-INDUCED LDL OXIDATION

SYNERGISTIC MIXTURES OF GARLIC AND LYCOPENE FOR PREVENTING LDL OXIDATION

CROSS REFERENCE TO RELATED APPLICATION

The present application is the national stage under 35 U.S.C. 371 of PCT/IL99/00062, filed Jan. 31, 1999.

The present invention concerns a composition containing lycopene and garlic. The present invention more particularly concerns a synergistic mixture of lycopene and garlic and its use in the prevention of LDL oxidation and preparing pharmaceutical or dietary compositions for arresting the progression of atheroclerosis.

BACKGROUND OF THE INVENTION

Atherosclerosis is the cause of death in more than 50% of people in Western Societies (Davies MJ and Woolf N. *Atherosclerosis: what is it and why does it occur? Br Heart J* 69:S3, 1993). In addition, it results in significant cardiac morbidity, such as anginal syndromes, myocardial infarctions, ischemic cardiomyopathy, sudden cardiac death, cerebrovascular accidents, and peripheral vascular disease. Indisputable evidence for an association between coronary heart disease (CHD) and risk factors, such as arterial hypertension, cigarette smoking and hyperlipidemia, has been derived from a variety of epidemiological studies. Of all the risk factors established thus far, lipid disorders play a key role in the pathogenesis of atherosclerotic vascular disease, especially of CHD. Many epidemiological and clinical trials have demonstrated the powerful association between hyperlipidemia and the widespread incidence of CHD. The Framingham Heart Study (Castell WP, Anderson K, Wilson PW., Levy D. *Lipids aid risk of coronary heart disease. The Framingham Study. Ann Epidemiol* 2(1–2): 23–28, 1992), which has been continuous since 1984, showed that hypercholesterolemia is a major contributor to the development of CHD. The link between atherosclerosis and cholesterol has been confirmed by a number of clinical trials.

Fats are insoluble in the aqueous medium of the blood. Thus, transport of the lipids triglycerides, phospholipids and cholesterol occurs exclusively by way of lipid-protein complexes, the lipoproteins. The lipoproteins are classified into 4 broad classes-chylomicrons, very low density lipoprotein (VLDL), low density lipoprotein (LDL), and high density lipoprotein (HDL), which differ in their composition, size, and potential atherogenicity.

Measurement of total cholesterol level in plasma reflects the sum of cholesterol being transported in each individual lipoprotein. However, LDL and HDL are the main cholesterol carriers in plasma and only a small fraction of cholesterol is carried in VLDL or in the chylomicrons.

Atherosclerosis is a gradual pathological process, which is characterized by an accumulation of lipid filled macrophages (foam cells), and smooth muscle cells resulting in lesions that thicken and harden the arterial wall. The main source for the cholesterol accumulating in the foam cells is the circulating LDL. There is evidence from numerous epidemiological and clinical studies that LDL, as the carrier of ca. 70% of the total cholesterol in plasma, are the most potent atherogenic lipoproteins. Their elevation carries a particular risk, and reduction in LDL cholesterol constitutes a diminished atherosclerotic risk. The Lipid Research Clinics Coronary Primary Prevention Trial (LRC-CPPT) had for the first time presented firm proof that in man, a lowering of LDL cholesterol level reduces the rate of myocardial infarcton and infarction mortality.

Nearly all cells, including macrophages, take up exogenous cholesterol via LDL-receptors. Increase in cell cholesterol content, however, result in down-regulation of LDL receptor number, thereby protecting cells from excessive accumulation of cholesterol by way of this pathway. It was shown that chemical or biological modification, including oxidation of LDL, results in increased uptake of the modified lipoprotein by way of other cell surface receptors, termed scavenger receptors. These receptors are present on macrophages and endothelial cells.

Oxidative modification of LDL is thought to play a causal role in atherosclerosis: (see e.g. Steinberg D, Parthasarathy S., Carew T. E., Khoo J. C. and Witztum J. L, "Beyond cholesterol: modifications of low-density lipoprotein that increase its atherogenicity", N. Engl. J. Med. 1989, 320: 915–924, Haberland M. E. and Fogelman A. M., "The role of altered lipoproteins in the pathogenesis of atherosclerosis", Am. Heart. J. 1987; 113: 573–577, and Witztun J. L., "The oxidation hypothesis of atherosclerosis", Lancet. 1994; 344, 793). It is believed, accordingly, that prevention of LDL oxidation by antioxidants may arrest the progression of atherosclerosis. (see e.g., Aviram M. Beyond cholesterol: Modification of lipoproteins and increased pitherogenicity. In Atherosclerosis, Inflammation and and Thrombosis (GG Neri Serneri, GF Geusini, R. Abbate and D. Prisco eds) Scientific Press-Florence, Italy, pp: 15–36, 1993, Aviram M. Oxidized low density lipoprotein (OX-LDL) interaction with macrophages in atherosclerosis and the ocutioctberogenicity of antioxidants. Europ. J. Clin. Chem. Clin. Biochem. 34: 599–608, 1996).

The ability to prevent the development of atherosclerotic lesions would have major implications for the public health. Thus using therapeutic agents with plural effects, such as lowering cholesterol and inhibiting oxidative modification, might have beneficial effects over other individual agent.

Carotenoids are colored pigments with lipophilic properties, widely distributed in fruits and vegetables, (e.g. β-carotene in carrots and lycopene in tomatoes) and possess some antioxidant properties: (see e.g. Burton G. W., "Antioxidant action of carotenoids," 1989; J. Nutr. 119:109–111 and Krinsky N. I., "antioxidant functions of carotenoids", Free Rad. Biol. Med. 1989, 7: 617–635 (9–13)). Carotenoids are transported within circulating lipoproteins, and it was postulated that they participate in the protection of LDL from oxidative modification.

Carotenoids consumption was shown in previous epidemiological studies to be associated with reduced cardiovascular mortality (see e.g.: Kohlmeier L. and Hasting S. B., "Epidemiologic evidence of a role of carotenoids in cardiovascular disease prevention", Am. J. Clin. Nutr. 1995; 62: 137S–146S), although recent data did not demonstrate similar beneficial effect (see e.g., Hennekens C. H., Buring J. E., Manson J. E., Stampfer M, Rosier B., Cook N. R., Belanger C., LaMotte F., Gaziano J. M., Ridker P. M., Willett W. and Peto R, "Lack of effect of long-term supplementation with β carotene on the incidence of malignant neoplasms and cardiovascular disease", N. Engl. J. Med. 1996; 334: 1145–1149).

Reduced plasma lipid peroxidation was recently shown to be associated with increased consumption of tomatoes. Low levels of plasma carotenoids were shown to be associated with an increased risk of myocardial infarction, and recently it was demonstrated that the association between β-carotene and acute myocardial infarction depends on the polyunsaturated fatty acids status, and that feeding the all-trans isomer of β-carotene to cholesterol-fed rabbits attenuated the extent of their atherosclerosis, with no effect on LDL oxidizability ex vivo. Data on the ability of β-carotene supplementation in vitro or in vivo to protect LDL from oxidation are conflicting: some studies found an inhibitory effect of β-carotene supplementation on LDL oxidation, whereas several other did not find such effect.

Lycopene, the open chain analog of β-carotene, shares with it similar structure with an extended conjugated double bonds. In human plasma, lycopene and β-carotene are quantitatively the major carotenoids. Lycopene was shown to possess the greatest quenching ability of singlet oxygen among the various carotenoids (DiMascio P., Kaiser S. & Sies H., "Lycopene as the most efficient biological carotenoid singlet oxygen quencher," Arch. Biochem. Biophys., 1989, 274: 532–538) and it was shown to be at least twice as effective antioxidant as β-carotene in protecting blood lymphocytes form $NO_2$ radical damage (Bohrn F., Tinkler J. H., and Truscott T. G., "Carotenoids protect against cell membrane damage by the nitrogen dioxide radical", Nature Medicine, 1995, 2: 98–99).

We have recently demonstrated a protective effect of tomatoes lycopene against oxidative modification of LDL. This protection of LDL by lycopene exceeded the protection exhibited by β-carotene, was selective only to LDL's with high vitamin E content and was shown when the carotene was present in combination with vitamin E. (see e.g., Fuhrnan B, Ben Yaish L, Attiasy. Hayek T, Aviram M. Tomatoes lycopene and β-carotene inhibit low density lipoprotein oxidation and this effect depends on the lipoprotein vitamin E content. Nutr Metab. Cardiovasc. Dis 7: 433–443, 1997). Furthermore, we have also demonstrated that dietary supplementation of lycopene acts as moderate hypocholesterolemic agent secondary to its inhibitory effect on cellular cholesterol synthesis (see e. . Fuhnnan B., Elis A., Aviram M., Hypocholesterolemic effect of lycopene and β-carotene is related to suppression of cholesterol synthesis and augmentation of LDL receptor activity in macrophages. Bichem, Biophys Res. Commun 233: 658–662 (1997).

The therapeutic actions of garlic and its constituents has been widely reported. See, for example: K. G. Agarwal, Med. Res. Rev., Vol 16 (1996) pp. 111–124; L. D. Lawson, *Bioactive organsulfur Compounds of Garlic and their role in Reducing Blood Lipids*, pp. 308–330 in: A. D. Kirighom and M. F. Balandrin (Editors), Human Medicinal Agents form Plants, American Chemical Society Books, Washington, 1983.; S. Eilat, et. al., Coronary Artery Disease, Vol. 6 (1995) 985–990; Anonymous, Deodorized (aged) Garlic Products Versus Conventional Allicin Containing Garlic Products: Summary of Current Knowledge, Commercial White Paper issued by Wakunanaga of America (date unknown).

Most of the significant results of garlic on cholesterol were obtained from animal studies. Allicin has a beneficial effect on the serum lipid profile in hyperlipidernic rabbits (Eilat, S., Oeataicher, Y., Rabinkov, A., et al. Alteration of lipid profile in hyperlipidemnic rabbits by allicin, an active constituent of garlic, Coron. Artery Dis. 6:985–90, 1995.). Similar results were reported in rats (Lata, S., Saxena, K. K., Bhasin, V., et al. Beneficial effects of Allium sativum, Allium cepa and Commiphora mukul on experimental hyperlipidemia and atherosclerosis-a comparative evaluation, J-Postgrad-Med. 37: 132–5, 1991). Hypercholesterolemia induced by cholesterol-feeding in rats was significantly reduced by garlic. In addition, significant effect were found in protecting the enzvmes of the glutathione dependent peroxide detoxification system, which are strongly impaired under hypercholesterolemia (Heinle, H. and Betz, E. Effects of dietary garlic supplementation in a rat model of atherosclerosis, Arzneimittelforschung. 44: 614–7, 1994). The effect of garlic on the human serum lipid profile has been the subject of controversy. According to some views there is inadequate scientific justification for garlic supplementation (Kleijnen, J., Knipschild, P., and ter Riet, G. Garlic, onions and cardiovascular risk factors. A review of the evidence from human experiments with emphasis on commercially available preparations, (Br. J. Clin. Pharmacol. 28: 35–44, 1989.) although this view was changed with the publications of more recent studies. Very mild reduction in cholesterol was found in aged people (aged 70 years and over) consuming garlic powder (Brosche, T., Platt, D., and Dorner, H. The effect of a garlic preparation on the composition of plasma lipoproteins and erythrocyte membranes in geriatric subjects, Br J Clin Pract Symp Suppl. 69: 12–9, 1990.) On the other hand, 50 medical students of the age group of 17 to 22 took 10 gm of raw garlic daily after breakfast for two months. There was a significant decrease in serum cholesterol and an increase in clotting time and fibrinolytic activity (Gadkari, J. V. and Joshi, V. D. Effect of ingestion of raw garlic on serum cholesterol level, clotting time and fibrinolytic activity in normal subjects, J-Postgrad-Med. 37: 128–31, 1991.) The effect of the consumption of a fresh clove of garlic on platelet thromboxane production was also examined. After 26 weeks of garlic consumption, there was an approximately 20% reduction of serum cholesterol and about 80% reduction in serum thromboxane (Ali, M. and Thomson, M. Consumption of garlic clove a day could be beneficial in preventing thrombosis, Prostaglandins-Leukot. Essent. Fatty Acids. 53:211–2, 1995. This and other results point that garlic helps in mild cases of hypertension and byperlipidaemia (Auer, W., Eiber, A., Hertkom, E., et al. Hypertension and hyperlipidaemia: garlic helps in mild cases, Br J Clin Pract Symp Suppl. 69: 3–6, 1990.) Only one not very detailed, study was done with Garlic ginkgo combination (Kenzelmann, R. and Dade, F. Limitation of deterioration of lipid parameters by a standardized garlic-ginkgo combination product. A multicenter placebo controlled double blind study, Arzneimittelforschung. 43: 978–81, 1993).

Several studies with standardized garlic diet in proximity to 900 mg/day revealed a significant but very mild effect on serum cholesterol. For example low-density lipoprotein cholesterol was reduced by 11% by garlic treatment and 3% by placebo in one study (Jain, A. K., Vargas, R., Gotzkowsky, S., and McMahon, F. G. Can garlic reduce levels of serum lipids? A controlled clinical study, Am-J-Med. 94:632–5, 1993.) In a second study lowering of total cholesterol values by an average of 12% and triglyceride values by an average of 17% was reported (Mader, F. H. Treatment of hyperlipidaemia with garlic-powder tablets. Evidence from the German Association of General Practitioners' multicentric placebo-controlled double-blind study, Arzneimittelforschung. 40: 1111–6, 1990.) In a third study a 12% reduction with garlic therapy as compared to placebo alone was reported (Silagy, C. and Neil, A. Garlic as a lipid lowering agent—a meta-analysis, J-R-Coll-Physicians-Lond. 28: 39–45, 1994.) An additional study concluded that dietary supplementation with aged garlic extract has beneficial effects of the lipid profile and blood pressure of moderately hypercholesterolemic subjects (Steiner, M., Khan, A. H., Holbert, d., and Lin, R. I. A double-blind crossover study in moderately hypercholesterolemic men that compared the effect of aged garlic extract and placebo administration on blood lipids, Am-J-Clin-Nutr. 64: 866–70, 1996.) In a placebo controlled study the drug group received 900 mg garlic powder per day, equivalent to 2,700 mg of fresh garlic. During the therapy, the drug group showed significantly lower total cholesterol, triglycerides and blood pressure than those of the placebo group (Vorberg, G. and Schneider, B. Therapy with garlic: results of a placebo-controlled, double-blind study, Br J Clin. Pract. Symp. Suppl. 69: 7–11, 1990.) Meta-analysis of the controlled trials of garlic to reduce hypercholesterolemia showed a significant reduction in total cholesterol levels. The best available evidence suggests that garlic, in an amount approximating one half to one clove per day, decreased total serum cholesterol levels by about 9 in the groups of patients studied (Warshafsky, S., Kamer, R. S., and sivak, S. L. Effect of garlic on total serum cholesterol, A meta-analysis (Ann-Intem-Med. 119: 599–605 m 1993.)

However such moderate results may bring to the conclusion that garlic was less effective in reducing total cholesterol than suggested by previous meta-analyses. Possible explanations are publication bias, overestimation of treatment effects in trials with inadequate concealment of treatment allocation. The authors of this recent review concluded that meta-analyses should be interpreted critically and with particular caution if the constituent trials are small (Neil, H. A., Silagy, C. A., Lancaster, T., et al. Garlic powder in the treatment of moderated hyperlipidaemnia: a controlled trial and meta-analysis, J-R-Coll-physicians-Lond. 30: 329–34, 1996). Another study has found no demonstrable effect of garlic ingestion on lipids and lipoproteins (Simons, L. A., Balasubramaniam, S., von Konigsmark, M., et al. On the effect of garlic on plasma lipids and lipoproteins in mild hypercholesterolaemia, Atherosclerosis. 113: 219–25, 1995).

Cultured rat hepatocytes continually synthesize cholesterol from radiolabeled acetate during a 24 h incubation period and export it, presumably as VLDL to the culture medium. Mevastatin inhibits cholesterol biosynthesis by 90%. Incubation of the cultures with water-soluble extracts of garlic powder (kwai, Sapec) diminish cholesterol biosynthesis (20–25%) as well as its export into the medium (30–355). The $IC_{50}$-value is 90 micrograms/ml. Between 0.25 and 10 mg/ml the average maximal inhibition amounts to about 23%. Cytotoxicity of the extracts is apparent at concentration above 125 mg/ml only. Pure allicin before, or after incubation with alliinase (conversion to allicin) in concentration corresponding to its content in the extracts does not exert any inhibition. Replacement of $^{14}C$-acetate by $^{14}C$-mevalonate omaiis the inhibitory effect. The activity of HMGCoA (hydroxyrnethylglutaryl-CoA) reductase is significantly reduced by garlic extracts at 50 microgramslml. At higher concentrations fatty acid synthetase, cholesterol 7 alpha-hydorxylase and cholesterol acyltransferase are slightly inhibited. Fatty acid synthetase is the only one of these enzymes which is inhibited by allicin at very high concentration. These results demonstrate that water-soluble garlic extracts diminish hepatic cholesterol biosynthesis, thus contributing to the reduction of blood cholesterol. The main target site seems to be HMGCoA-reductase. The actual active principle(s) is still unknown (Gebhardt, R. and Beck, H. Differential inhibitory effects of garlic-derived organo-sulfur compounds on cholesterol biosynthesis in primary rat hepatocyte cultures, Lipids. 31: 1269–76, 1996; Gebhardt, R Multiple inhibitory effects of garlic extracts on cholesterol biosynthesis in hepatocytes, Lipids. 28: 613–9, 1993; Gebhardt, R Inhibition of cholesterol biosynthesis by a water-soluble garlic extract in primary cultures of rat hepatocytes, Arzneimittelforschung. 41: 800–4, 1991). Inhibition of cholesterol synthesis was shown in vitro by extracts and isolated compounds prepared from garlic and wild garlic (Sendl, A., Schliack, M., Loser, R., Stanislaus, F., and Wagner, H. Inhibition of cholesterol synthesis in vitro by extracts and isolated compounds prepared from garlic and wild garlic, Atherosclerosis. 94: 79–85, 1992).

The antioxidant properties of garlic which have been demonstrated in vitro led to a study on the effects of garlic supplements on lipoprotein oxidation susceptibility in humans. Ten healthy volunteers were given 600 mg/d of garlic powder (6 tablets of Kwai) for two weeks in a placebo-controlled, randomized, double-blind crossover trial. It was found that although serum lipid and lipoprotein levels were not lowered in this short time period, the ex vivo susceptibility of apolipoprotein B-containing lipoproteins to oxidation was significantly decreased (−34%) (Phelps, S. and Harris, W. S. Garlic supplementation and lipoprotein oxidation susceptibility, Lipids. 28: 475–7, 1993).

After all of the above voluminous studies nowhere is it suggested to use a mixture of garlic and lycopene to prevent and/or combat atherosclerosis.

OBJECTIVES

It is an objective of the present invention to provide a novel mixture of lycopene and garlic. It is an objective of the present invention to provide a synergistic mixture of lycopene and garlic active in blocking the oxidation of LDL and/or atherosclerosis and reduce the cholesterol levels in plasma. An additional objective of the present invention is the use of the above described mixture to prepare a pharmaceutical or dietary composition for arresting the progression of atherosclerosis.

SUMMARY OF THE INVENTION

In accordance with the present invention there is provided a synergistic pharmaceutical or dietary composition containing lycopene and garlic. The present invention also provides an improved method to block the oxidation of LDL, to arrest the progress of atherosclerosis, a hypercholesterolemia therapeutic agent and a method for the prevention or treatment of atherosclerosis using and/or applying said composition.

BRIEF DESCRIPTION OF THE DRAWING

FIGS. 1, 2 and 5 are graphs showing the effects of a combination of garlic and lycopene on copper ions-induced LDL Oxidation.

DETAILED DESCRIPTION OF THE INVENTION

The source of lycopene can be either contained in tomato oleoresin, lycdpene extracted from tomato, or synthetic lycopene.

The source of the garlic can be selected from the group consisting of whole garlic, allicin, garlic powder, non-polar solvent extracts of fresh crushed garlic, aged deodorized garlic extract, and enisxes of these. A preferred source is garlic powder containing between 0.2% to 2.0% allicin and preferably containing 0.5% to 1.2% allicin.

The garlic and lycopene can be present in relative parts by weight of 10,000 to 1 to 1 to 10,000; preferably 500 to 1 to 1 to 500, and most preferably 100 to 1 to 1 to 100.

The garlic and lycopene can be the only ingredients present. However, it is sometimes preferred to mix in compounds such as dietary components, additives, excipients, bonding agents, coatings, preservatives, and mixtures of these.

The garlic lycopene mixture may be contained in a dosage form selected from the group consisting of tablets, caplets, vegecaps, and hard shell gelatin capsules.

The mixture of garlic and lycopene has been found useful in preparing pharmaceutical or dietary compositions for arresting the progression of atherosclerosis, as a hypercholesterolemic therapeutic agent, and a method for synergistically blocking the oxidation of LDL in serum.

GENERAL EXPERIMENTAL PROCEDURE

LDL was separated from human plasma by discontinuous density gradient ultracentrifugation and dialyzed against saline: EDTA (1 mM). Before oxidation LDL was diluted in PBS to 100 ug protein/ml, and dialyzed overnight against PBS at 4° C.

LDL was oxidized by a metal ion dependent mechanism, by incubation for 24 hours at 37° C. with 5 uM $CuSO_4$ freshly prepared as well as by determination of the thiobarbituric acid reactive substance (TBARS).

LDL was also oxidized in a metal ions independent system by incubaiton at 37° C. with a radical generating compound, 2-2 azobis, 2-aminidinopropane hydrochloride (AAPH, 5mM).

Lycopene, as well as tomato oleoresin containing 5% lycopene, were dissolved in tetrahydrofuran (THF), 0.5 mg/ml stock solution for pure lycopene, and 10 mg/ml stock solution for the oleoresin.

Garlic powder was extracted with water, dried, and resolubilized in water at a concentration of 0.25 mg of allicin equivalentsml for a stock solution.

EXAMPLE 1

Figure 2A:
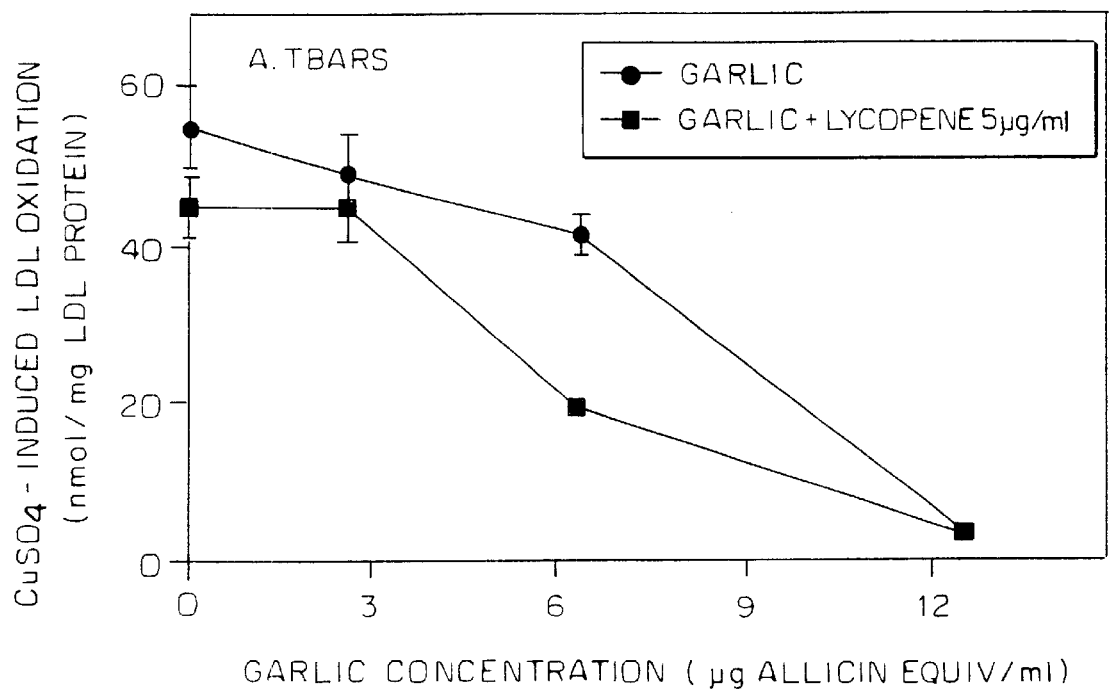
Figure 2B:
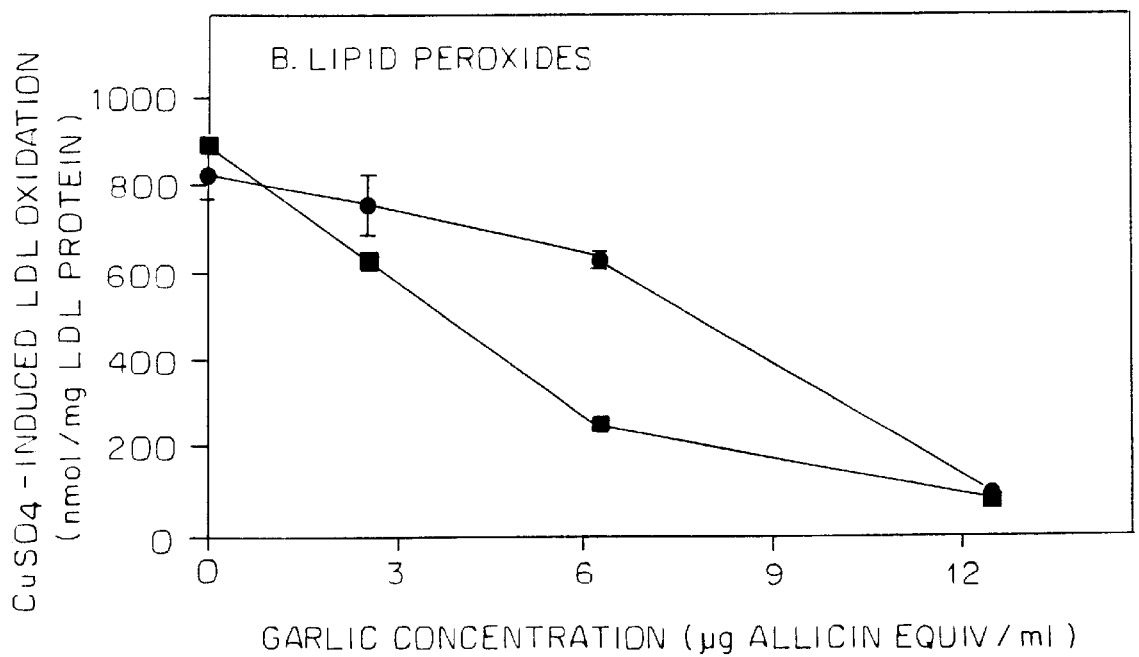

The synergistic effects of a combination of garlic and lycopene on copper ions-induced LDL oxidation was studied. Details are shown in Table 1, affording the individual components of the Abbott Equation used to calculate synergism as follows:

$$A + B \left(\frac{AB}{100}\right) = \text{Expected Control}$$

where A=Percent Control of garlic alone
B=Percent Control of Lycopene alone
and $$synergism = \frac{I_F}{I_E}$$

where $I_F$=Actual control in Percent
$I_E$=Expected control in Percent
and synergism is proven if the ratio of $$\frac{I_F}{I_E}$$

is significantly greater than 1.
FIGS. 1 & 2 shows the synergism

EXPERMENT 2

Figure 3A:
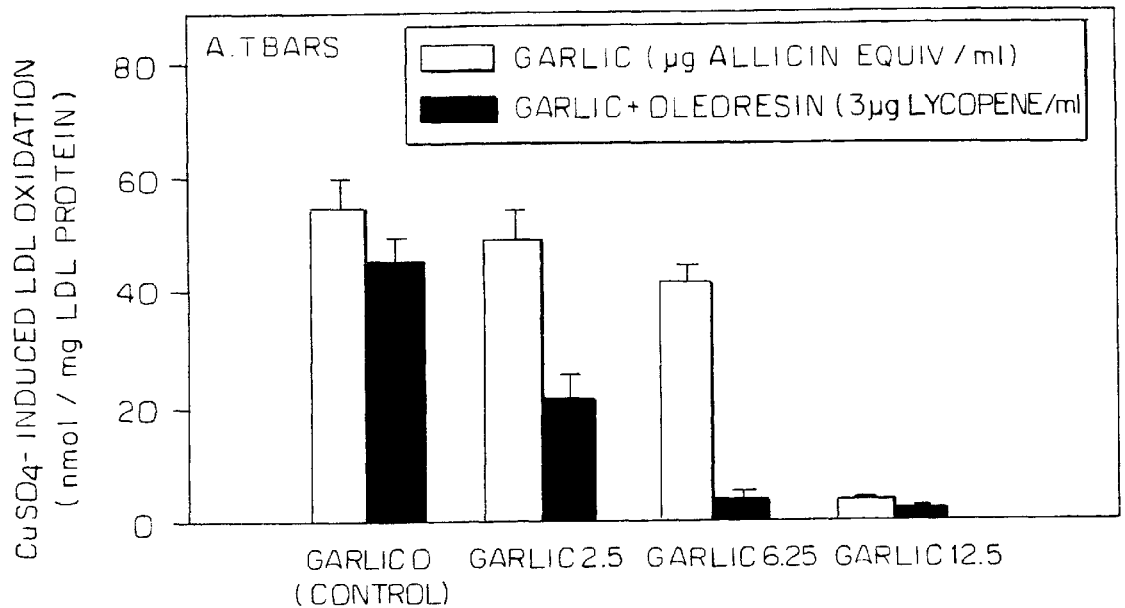
FIGS. 3, 4 and 6 are graphs showing the effect of a combination of garlic and tomato oleoresin on copper ions-induced LDL oxidation.
Figure 3B:
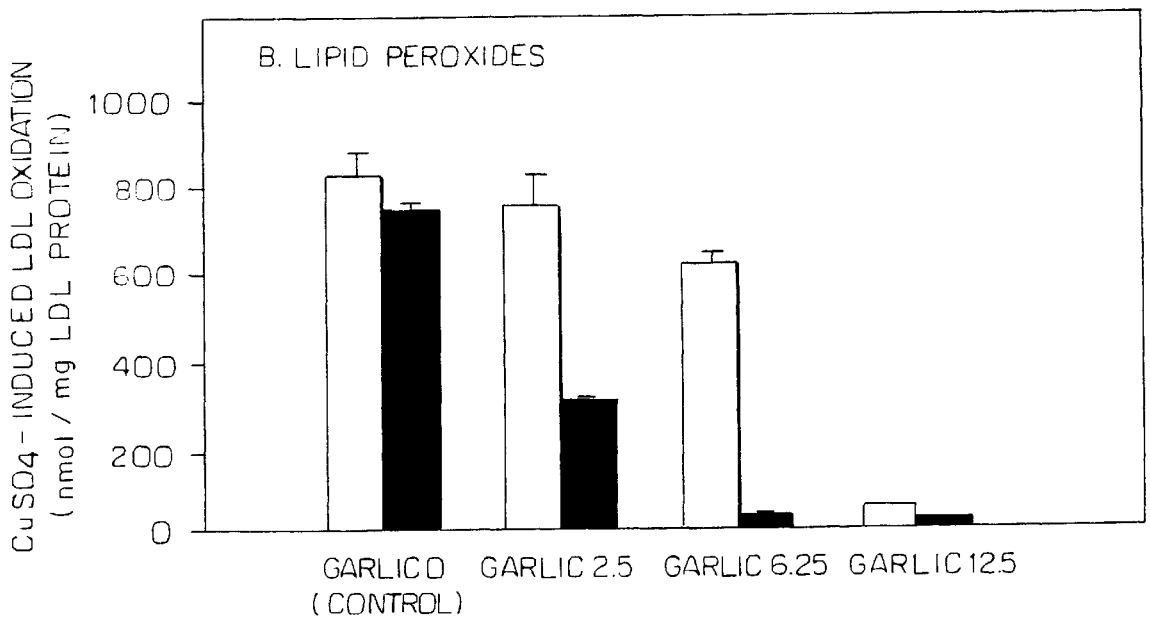
Figure 4A:
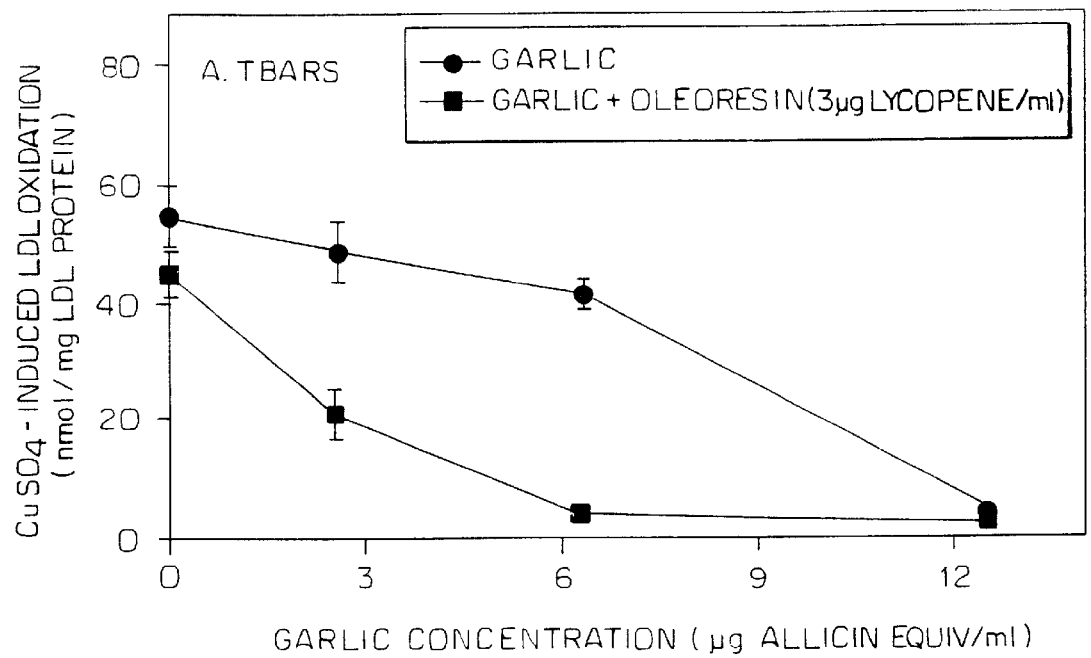
Figure 4B:
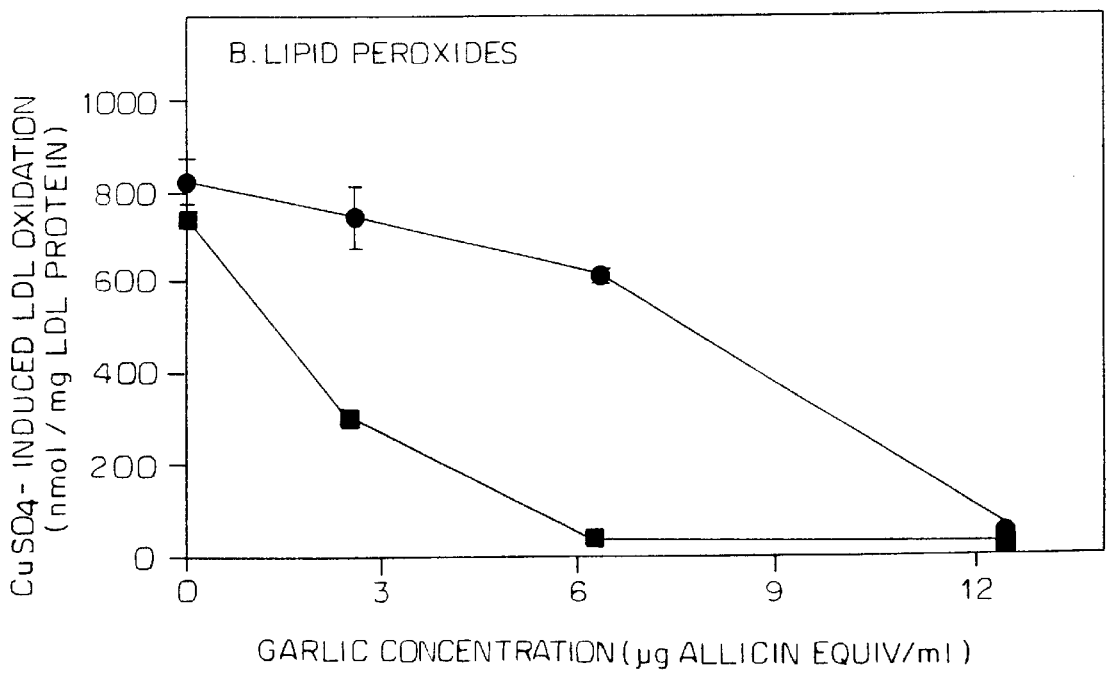

Following the method of Experiment 1, the synergistic effect of a combination of garlic and lycopene as in Experiment 1; but using tomato oleoresin was run. Results are shown in Table 1 and FIGS. 3 and 4.

EXAMPLE 3

Following the method of Example 1, the synergistic effect of a mixture of garlic and tomato oleoresin on AAPH-induced LDL oxidation was checked.

EXAMPLE 4

Figure 5:
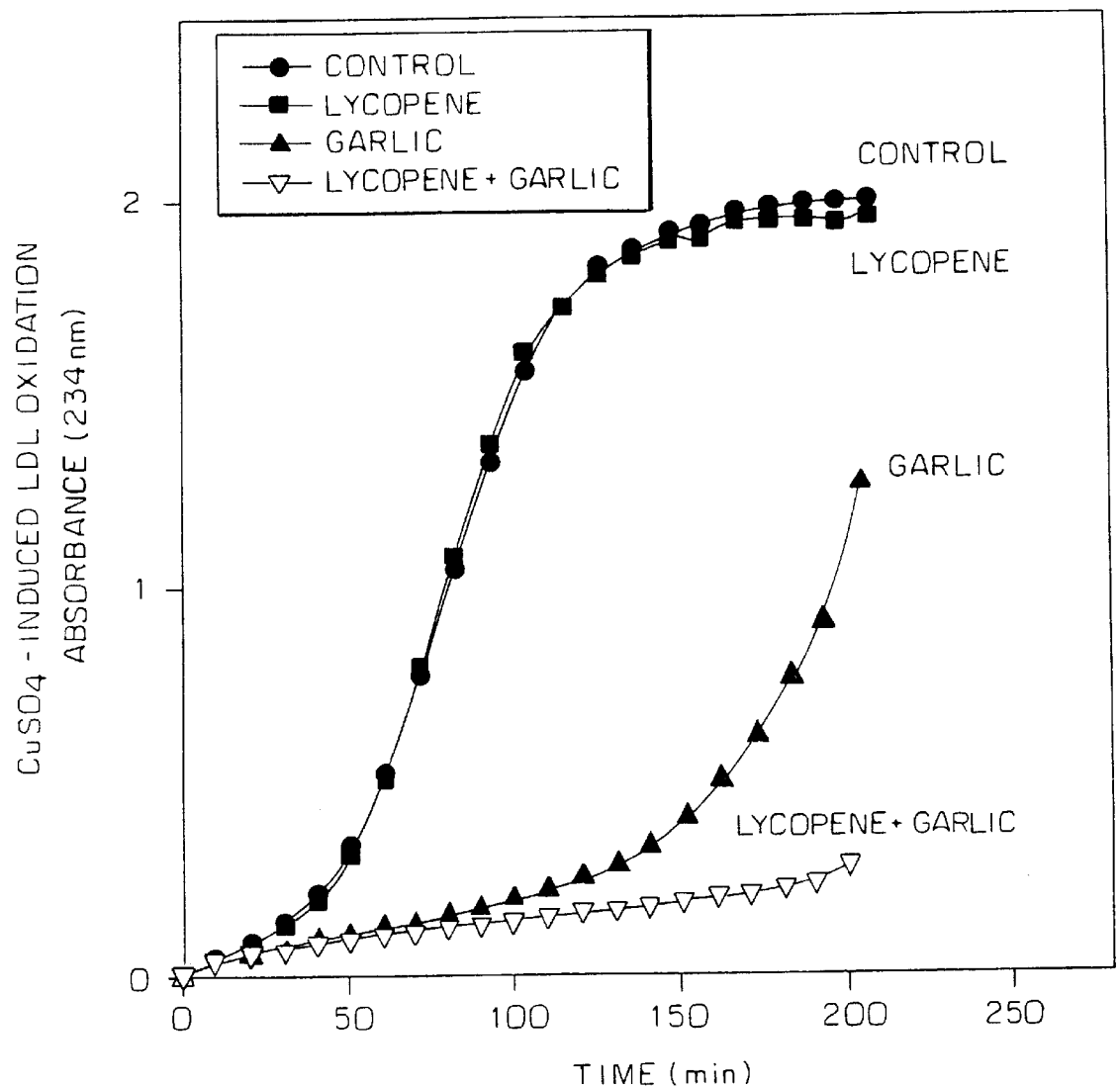

The kinetic study of the effect of the mixture of Experiment 1 was run to determine the prolonged log time. Details, shown in FIG. 5 found a retardation of 200 minutes for the mixture compared with 90 minutes for garlic alone.

EXAMPLE 5

Figure 6:
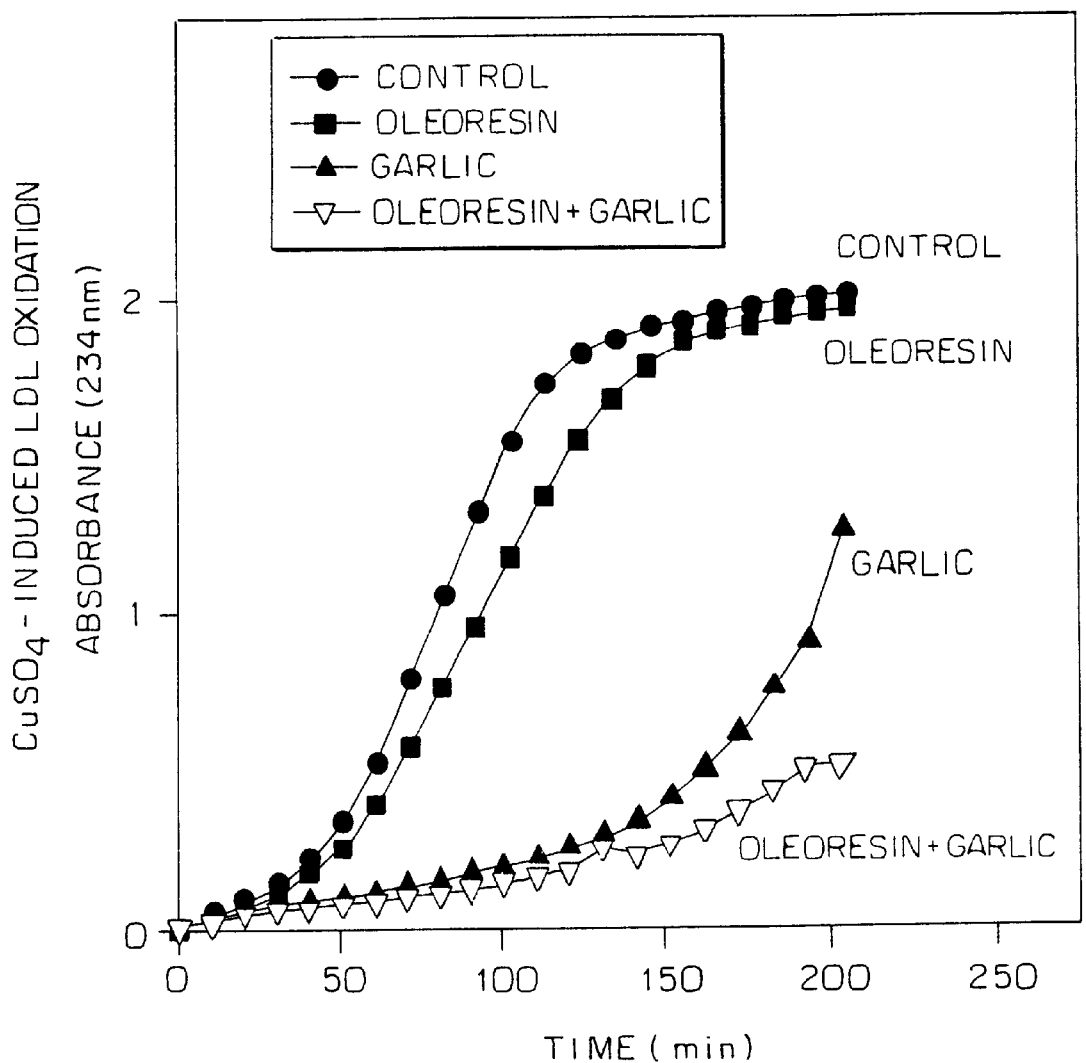

A similar kinetic study of the mixture of Experiment 2 was also run; and found the same log time for the mixture. Details are shown in FIG. 6.

TABLE I

DATA FROM EXPERIMENTS 1–3
FITTED TO THE ABBOTT EQUATION

| Experiment | A | B | $I_E$ | $I_F$ (TBARS) | $I_E$ (lipids) | $I_F/I_E$ (TBARS) | $I_F/I_E$ (lipids) |
|---|---|---|---|---|---|---|---|
| 1 | 25[a] | 18[b] | 38.5 | 64 | 72 | 1.66 | 1.87 |
| 2 | 0[c] | 0[d] | 0 | 54 | 60 | ∞ | ∞ |
| 3 | 26[a] | 18[e] | 39.3 | 68 | 50 | 1.73 | 1.27 |

[a]6.25 allicin equiv/ml
[b]5 μg/ml
[c]2.5 allicin equiv/ml
[d]3 μg lycopene/ml
[e]4.5 μg/ml

What is claimed is:

1. A synergistic Pharmaceutical or dietary composition which comprises lycopene and garlic, and optionally also comprises at least one of dietary components, additives, excipients, binding agents, coatings, and preservatives.

2. A composition in accordance with claim 1 wherein the lycopene is contained in tomato oleoresin.

3. A composition in accordance with claim 1 which comprises synthetic lycopene.

4. A composition in accordance with claim 1 wherein the garlic is selected from the group consisting of whole garlic, allicin, garlic powder, non-polar solvent extracts of fresh crushed garlic, aged deodorized garlic extract, and mixtures of these.

5. A composition in accordance with claim 4 wherein the garlic is garlic powder standardized on an allicin content between 0.2% to 2.0%.

6. A composition in accordance with claim 5 wherein the garlic powder is standardized on an allicin content between 0.5% to 1.2%.

7. A composition in accordance with claim 1 wherein the relative parts by weight of garlic to lycopene is 10,000 to 1; to 1 to 10,000.

8. A composition in accordance with claim 7 wherein the relative parts by weight of garlic to lycopene is 500 to 1; to 1 to 500.

9. A composition in accordance with claim 7 wherein the relative parts by weight of garlic to lycopene is 100 to 1; to 1 to 100.

10. A composition in accordance with claim 1 wherein the lycopene and garlic mixture are contained in dosage forms selected from the group consisting of tablets, caplets, vegecaps, and hard shell gelatin capsules.

11. A synergistic hypercholesterolemia therapeutic agent which contains lycopene and garlic as effective ingredients, and optionally further comprising at least one of dietary components, additives, excipients, binding agents, coatings and preservatives.

12. An agent in accordance with claim 11 wherein the lycopene is contained in tomato oleoresin.

13. An agent in accordance with claim 11 which comprises synthetic lycopene.

14. An agent in accordance with claim 11 wherein the garlic is selected from the group consisting of whole garlic, allicin, garlic powder, non-polar solvent extracts of fresh crushed garlic, aged deodorized garlic extract, and mixtures of these.

15. An agent in accordance with claim 14 wherein the garlic is garlic powder standardized on and allicin content between 0.2% to 2.0%.

16. An agent in accordance with claim 11 wherein the garlic powder is standardized on an allicin content between 0.5% to 1.2%.

17. An agent in accordance with claim 11 wherein the relative parts by weight of garlic to lycopene is 10,000 to 1; to 1 to 10,000.

18. An agent in accordance with claim 17 wherein the relative parts by weight of garlic to lycopene is 500 to 1; to 1 to 500.

19. An agent in accordance with claim 17 wherein the relative parts by weight of garlic to lycopene is 100 to 1; to 1 to 100.

20. An agent in accordance with claim 11 wherein the lycopene and garlic mixture are contained in a matrix selected from the group consisting of tablets, caplets, vegecaps, and hard shell gelatin capsules.

21. A method for inhibiting development or treatment of atherosclerosis in a mammal, said method comprising administering an effective amount of a synergistic mixture lycopene and garlic to said mammal in need of such inhibiting or treatment, and wherein said mixture optionally also includes at least one of dietary components, additives, excipients, binding agents, coatings, and preservatives.

22. A method for inhibiting development of or treatment of atherosclerosis in a mammal, said method comprising administering an effective amount of a synergistic mixture lycopene and garlic to said mammal in need of such inhibiting or treatment, and wherein said mixture optionally also includes at least one of dietary components, additives, excipients, binding agents, coatings, and preservatives, wherein the lycopene is contained in tomato oleoresin.

23. A method for inhibiting development of or treatment of atherosclerosis in a mammal, said method comprising administering an effective amount of a synergistic mixture lycopene and garlic to said mammal in need of such inhibiting or treatment, and wherein said mixture optionally also includes at least one of dietary components, additives, excipients, binding agents, coatings, and preservatives, wherein said lycopene comprises synthetic lycopene.

24. A method for inhibiting development of or treatment of atherosclerosis in a mammal, said method comprising administering an effective amount of a synergistic mixture lycopene and garlic to said mammal in need of such inhibiting or treatment, and wherein said mixture optionally also includes at least one of dietary components, additives, excipients, binding agents, coatings, and preservatives, wherein the garlic is selected from the group consisting of whole garlic, allicin, garlic powder, non-polar solvent extracts of fresh crushed garlic, aged deodorized garlic extract, and mixtures of these.

25. A method in accordance with claim 24 wherein the garlic powder standardized on and allicin content between 1.2% to 2.0%.

26. A method in accordance with claim 24 wherein the garlic powder is standardized on an allicin content between 0.5% to 1.2%.

27. A method for inhibiting development of or treatment of atherosclerosis in a mammal, said method comprising administering an effective amount of a synergistic mixture lycopene and garlic to said mammal in need of such inhibiting or treatment, and wherein said mixture optionally also includes at least one of dietary components, additives, excipients, binding agents, coatings, and preservatives, wherein the relative parts by weight of garlic to lycopene is from 10,000 to 1 to 1 to 10,000.

28. A method in accordance with claim 27 wherein the relative parts by weight of garlic to lycopene is 500 to 1; to 1 to 500.

29. A method in accordance with claim 27 wherein the relative parts by weight of garlic to lycopene is 100 to 1; to 1 to 100.

30. A method for inhibiting development of or treatment of atherosclerosis in a mammal, said method comprising administering an effective amount of a synergistic mixture lycopene and garlic to said mammal in need of such inhibiting or treatment, and wherein said mixture optionally also includes at least one of dietary components, additives, excipients, binding agents, coatings, and preservatives, wherein the lycopene and garlic mixture is contained in a matrix selected from the group consisting of tablets, caplets, vegecaps, and hard shell gelatin capsules.

31. A method for blocking the oxidation of LDL in serum which comprises contacting said serum with a synergistic composition containing lycopene and garlic, and wherein said composition optionally also comprises at least one of dietary components, additives, excipients, binding agents, coatings, and preservatives.

32. A method in accordance with claim 31 wherein the lycopene is contained in tomato oleoresin.

33. A method in accordance with claim 31 which comprises synthetic lycopene.

34. A method in accordance with claim 31 wherein the garlic is selected from the group consisting of whole garlic, allicin, garlic powder, non-polar solvent extracts of fresh crushed garlic, aged deodorized garlic extract, and mixtures of these.

35. A method in accordance with claim 34 the garlic is garlc powder standardized on an allicin content between 1.2% to 2.0%.

36. A method in accordance with claim 34 wherein the garlic powder is standardized on an allicin content between 0.5% to 1.2%.

37. A method in accordance with claim 31 wherein the relative parts by weight of garlic to lycopene is 10,000 to 1; to 1 to 10,000.

38. A method in accordance with claim 37 wherein the relative parts by weight of garlic to lycopene is 500 to 1; to 1 to 500.

39. A method in accordance with claim 37 wherein the relative parts by weight of garlic to lycopene is 100 to 1; to 1 to 100.

40. A method in accordance with claim 31 wherein the lycopene and garlic mixture are contained in a matrix selected from the group consisting of tablets, caplets, vegecaps, and hard shell gelatin capsules.

* * * * *